US006800462B2

(12) United States Patent
Wu et al.

(10) Patent No.: US 6,800,462 B2
(45) Date of Patent: Oct. 5, 2004

(54) PRODUCTION OF RECOMBINANT PROTEINS IN VIVO AND USE FOR GENERATING ANTIBODIES

(75) Inventors: Chung-Hsiun Wu, Taipei (TW); Rong-Hwa Lin, Taipei (TW); Pei-Ling Hsu, Little Rock, AR (US) 72212

(73) Assignee: AbGenomics Corporation, Taipei (TW)

( * ) Notice: Subject to any disclaimer, the term of this patent is extended or adjusted under 35 U.S.C. 154(b) by 138 days.

(21) Appl. No.: 10/077,210

(22) Filed: Feb. 14, 2002

(65) Prior Publication Data

US 2003/0049801 A1 Mar. 13, 2003

Related U.S. Application Data

(60) Provisional application No. 60/318,474, filed on Sep. 10, 2001.

(51) Int. Cl.$^7$ .................. C12P 21/08; G01N 33/531
(52) U.S. Cl. .................. 435/70.21; 424/184.1; 424/192.1; 436/547; 436/548; 514/44; 800/4; 800/5
(58) Field of Search .................. 424/184.1, 192.1; 514/44; 435/70.21; 436/547–548; 800/4–5

(56) References Cited

U.S. PATENT DOCUMENTS

| | | | | |
|---|---|---|---|---|
| 5,541,087 A | | 7/1996 | Lo et al. ................ | 435/697 |
| 5,698,679 A | * | 12/1997 | Nemazee ................ | 530/387.3 |
| 5,703,055 A | | 12/1997 | Felgner et al. ............. | 514/44 |
| 5,721,121 A | | 2/1998 | Etcheverry et al. ........ | 435/69.7 |
| 5,726,044 A | | 3/1998 | Lo et al. ................. | 435/69.7 |
| 5,843,678 A | | 12/1998 | Boyle ..................... | 435/7.1 |
| 5,959,171 A | | 9/1999 | Hyttinen et al. .......... | 800/2 |
| 6,001,973 A | | 12/1999 | Strom et al. ............. | 530/351 |
| 6,054,632 A | * | 4/2000 | Reid ..................... | 800/6 |
| 6,146,845 A | | 11/2000 | Kikly et al. ............. | 435/69.1 |
| 6,214,804 B1 | | 4/2001 | Felgner et al. ............ | 514/44 |
| 6,462,254 B1 | * | 10/2002 | Vernachio et al. ........ | 800/4 |

FOREIGN PATENT DOCUMENTS

WO  WO 00/29442  5/2000

OTHER PUBLICATIONS

Barry et al., "Production of Monoclonal Antibodies by Genetic Immunization," Biotechniques, 16(4):616–619 (1994).
Gregoriadis et al., "Liposome–mediated DNA vaccination," FEBS Letters, 402:107–110 (1997).
He et al., Intravenous Injection of Naked DNA Encoding Secreted flt3 Ligand Dramatically Increasese the Number of Dendritic Cells and Natural Killer Cells in Vivo, Human Gene Therapyy, 11:547–554 (Mar. 1, 2000).
Liu et al., "Hydrodynamics–based transfection in animals by systemic administration of plasmid DNA," Gene Therapy, 6:1258–1266 (1999).
Swimbanks et al., "Taiwan backs experience in quest for biotech success," Nature, 407:417–426 (Sep. 21, 2000).
Tang et al., "Genetic immunization is a simple method for eliciting an immune response," Nature, 356:152–154 (Mar. 12, 1992).
Templeton et al., "Improved DNA: liposome complexes for increased systemic delivery and gene expression," Nature Biotechnology, 15:647–652 (Jul. 1997).
Zhang et al., "High Levels of Foreign Gene Expression in Hepatocytes after Tail Vein Injections of Naked Plasmid DNA," Human Gene Therapy, 10:1735–1737 (Jul. 1, 1999).
Zhang et al., "Long–term expression of human alpha1–antitrypsin gene in mouse liver achieved by intravenous administration of plasmid DNA using a hydrodynamics–based procedure," Gene Therapy, 7:1344–1349 (2000).
Zhou et al., "Protective immunization against melanoma by gp100 DNA–HVJ–liposome vaccine," Gene Therapy, 6:1768–1773 (1999).
Brown. S. J. et al. Expression and ligand binding assays of soluble cytokine receptor–immunoglobulin fusions proteins. Prot. Exp. Purif. 1998, vol. 14, pps. 120–124.
Dwyer. M. A. et al. Expression and characterization of a DNase I–Fc fusion enzyme. J. Biol. Chem. Apr. 1999, vol. 274, No. 14, pps. 9738–9843.
Lundeberg, J. et al. Affinity Purification of specific DNA fragments using a lac repressor fusion protein. Genet. Anal. Techn. Appl. 1990, vol. 7, pps. 47–52.
Matsuda. T. et al. Establishment of the elisa fo murine soluble gp 130, a signal transducer for the IL–6 family cytokine, and its detection in the ascitic fluids of tumor–bearing mice. Biochem. Biophys. Res. Comm. 1994, vol. 202, No. 1, pps. 637–642.
Stewart. L.M. et al. Humanisation and characterization of PR1A3, a monoclonal antibody specific for cell–bound carcinoembryonic antigen. Cancer Immunol., Immunother. 1999, vol. 47, pps. 299–306.

* cited by examiner

Primary Examiner—David Saunders
(74) Attorney, Agent, or Firm—Fish & Richardson P.C.

(57) ABSTRACT

The invention is directed to methods of producing a protein by administering a nucleic acid encoding the protein to an animal. Following the administration of the nucleic acid to the animal, the protein is produced in vivo and is isolated by removing a biological sample from the animal. These methods allow for the rapid and efficient production and isolation of a protein encoded by any nucleic acid sequence of interest and can be used to generate antibodies that bind to the protein sequence.

38 Claims, 1 Drawing Sheet

PRODUCTION OF RECOMBINANT PROTEINS IN VIVO AND USE FOR GENERATING ANTIBODIES

RELATED APPLICATIONS

This application claims priority from U.S. provisional application serial No. 60/318,474, filed on Sep. 10, 2001, the content of which is incorporated herein by reference.

FIELD OF THE INVENTION

The invention relates to methods and compositions for producing proteins and generating antibodies.

BACKGROUND OF THE INVENTION

Antibodies are valuable tools for both basic research and the diagnosis and treatment of various diseases. Protein-specific binding antibodies allow for the precise identification and quantitation of a particular species of protein in a biological sample. In addition, the interaction between a protein and its binding antibody can modulate the activity or function of a protein. Modulation of the activity or function of a protein is particularly useful in treating a disease condition characterized by either excessive or insufficient activity of a given protein.

The generation of protein-specific antibodies frequently involves immunization using a purified form of a protein against which antibodies are desired. Providing sufficient quantities for immunization with a specific, properly folded protein is a common challenge in the field of antibody generation.

SUMMARY OF THE INVENTION

The invention is directed to methods of producing a protein by administering a nucleic acid encoding the protein to an animal. According to these methods, any nucleic acid sequence of interest can be administered to an animal. Following the administration of the nucleic acid to the animal, the protein is produced in vivo and can be isolated following the removal of a biological sample from the animal.

A protein produced according to these methods can be used to generate in a second animal an antibody that binds to a protein sequence of interest. In some instances, the methods include an initial isolation of the protein from the biological sample. This isolated protein is then used to immunize an animal. This invention thus permits the efficient generation of antibodies directed against a target amino acid sequence.

In one aspect, the invention includes a method of generating an antibody by performing the following steps: (1) administering to a first mammal a nucleic acid encoding a fusion protein and expressing the fusion protein in the first mammal, wherein the fusion protein contains a first amino acid sequence and a second amino acid sequence, and wherein the second amino acid sequence contains a first member of a specific binding pair; (2) removing from the first mammal a biological sample that contains the fusion protein; (3) binding a second member of the specific binding pair to the fusion protein via the first member of the specific binding pair to thereby isolate the fusion protein; and (4) administering the fusion protein to a second mammal, to thereby generate an antibody response in the second mammal against the first amino acid sequence of the fusion protein.

In one embodiment, the method also includes a step of cleaving the first amino acid sequence from the second amino acid sequence.

In one embodiment, the first member of the specific binding pair is a peptide of at least five amino acids in length. For example, the first member of the specific binding pair can be an Fc domain of an immunoglobulin.

The biological sample used in the method can include, for example, serum or a tissue lysate. The method can include an additional step of generating a lysate of the biological sample.

In one embodiment, the second member of the specific binding pair is an antibody, e.g., a monoclonal antibody.

The method can include an additional step of administering a protease inhibitor to the animal before removing the biological sample from the animal.

The method can also include an additional step of immobilizing the fusion protein.

In one embodiment, the first amino acid sequence of the fusion protein is identical to all or a portion of a naturally occurring human protein.

The method can include an additional step of isolating from the second mammal antisera containing an antibody that specifically binds to the first amino acid sequence of the fusion protein, wherein the antibody is produced in the second mammal following the administration of the fusion protein.

The method can include an additional step of removing a B lymphocyte from the second mammal and fusing the B lymphocyte in vitro with a second cell to form a hybridoma, wherein the hybridoma produces a monoclonal antibody that specifically binds to the first amino acid sequence of the fusion protein.

The method can include an additional step of removing components of the biological sample that are not bound to the second member of the specific binding pair, to thereby provide a purified fusion protein.

In another aspect, the invention features a method of generating an antibody by performing the following steps: (1) administering to a first mammal an isolated nucleic acid encoding a protein and expressing the protein in the first mammal; (2) removing from the first mammal a biological sample that contains the protein; and (3) administering the protein to a second mammal, to thereby generate an antibody response in the second mammal against the protein.

The protein used in the method can optionally be a fusion protein. The fusion protein can contain a first amino acid sequence and a second amino acid sequence, wherein the second amino acid sequence contains a first member of a specific binding pair. In one embodiment, the first member of the specific binding pair is a peptide of at least five amino acids in length. For example, the first member of the specific binding pair can be an Fc domain of an immunoglobulin.

The biological sample used in the method can include, for example, serum or a tissue lysate. The method can include an additional step of generating a lysate of the biological sample.

The method can include an additional step of isolating from the second mammal antisera containing an antibody that specifically binds to the protein, wherein the antibody is produced in the second mammal following the administration of the protein.

The method can include an additional step of removing a B lymphocyte from the second mammal and fusing the B lymphocyte in vitro with a second cell to form a hybridoma, wherein the hybridoma produces a monoclonal antibody that specifically binds to the protein.

An advantage of the invention is that it provides rapid and efficient methods for the production of large amounts of a protein or portion thereof in its native conformation. The purified protein can then be used in generating antibodies that bind to the corresponding native protein sequence. These production methods avoid the time-consuming, expensive, and laborious tasks associated with the in vitro production and purification of proteins.

Another advantage of the invention is that it avoids several of the difficulties associated with recombinant protein production in bacteria. Mammalian proteins expressed in bacteria lack post-translational modification and frequently do not possess their native conformation. In addition, some proteins cannot even be translated in some bacteria because some nucleic acid constructs contain codons that are rarely used in bacteria.

Unless otherwise defined, all technical and scientific terms used herein have the same meaning as commonly understood by those of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of a conflict in terminology, the present specification will control. In addition, the described materials and methods are illustrative only and are not intended to be limiting.

Other features and advantages of the invention will be apparent from the following detailed description and the claims.

DETAILED DESCRIPTION

The invention is directed to methods of generating an antibody against a protein of interest by administering to an animal a nucleic acid encoding the protein or a portion thereof. The protein or a portion thereof is produced within the animal, removed from the animal, and then used to immunize a second animal to generate an antibody against the protein. In some instances, the method includes a step of isolating the protein by use of an affinity reagent that specifically binds to the protein (e.g., binds to a portion of the protein engineered to contain an affinity tag).

Nucleic Acid Constructs

The invention encompasses the use of a variety of nucleic acid constructs encoding fusion proteins. The fusion proteins encoded by the nucleic acids described herein contain at least two heterologous amino acid sequences, designated a first amino acid sequence and a second amino acid sequence. Because these two amino acid sequences are heterologous, the sequence of the fusion protein thus differs from that of a naturally occurring protein.

The identity of the first amino acid sequence is essentially unlimited. The first amino acid sequence is generally a focus of the methods of the invention, in that a variety of applications can be carried out on this sequence, including but not limited to methods to generate antibodies that bind to the sequence. In one example, the first amino acid sequence is identical to all or a portion of a naturally occurring protein. Preferably, the first amino acid sequence is at least 6, 10, 25, 50, 100, or 200 amino acids in length. In another example, the first amino acid sequence contains an epitope that can be recognized by an antibody.

The second amino acid sequence of the fusion protein contains a sequence that permits the immobilization and/or purification of the fusion protein. Therefore, the second amino acid sequence contains a first member of a specific binding pair that can bind to a second member of the specific binding pair. In one example of a specific binding pair, the first member of the pair is a stretch of amino acids that is bound by the second member of the pair, e.g., an antibody such as a monoclonal antibody. One embodiment of such a binding pair is an immunoglobulin Fc constant region (first member of the specific binding pair) and an anti-immunoglobulin Fc constant region antibody (second member of the specific binding pair). In another example of a specific binding pair, the first member of the binding pair is a stretch of amino acids that is bound by a non-protein affinity agent. An example of such a specific binding pair is a poly-histidine tag (first member of the specific binding pair) and a nickel affinity reagent (second member of the specific binding pair). For example, a tag of 6–10 histidine residues, when included in a fusion protein, can be used to purify the fusion protein by nickel affinity chromatography (see, e.g., Copeland et al. (1996) Nature 379:162–165).

Amino acid sequences in addition to the first and second amino acid sequences described herein can be included in the fusion protein. For example, a targeting sequence can be used that directs trafficking of the fusion protein (e.g., the targeting sequence can direct the fusion protein to a specific cellular compartment, to the plasma membrane, or can direct secretion of the protein). In one example, the fusion protein contains a signal peptide sequence. A signal peptide sequence refers to a short (usually about 15–60 amino acids), continuous stretch of amino acids located at the amino-terminus of nascent secreted and membrane-bound polypeptides, which directs their delivery to various locations. Signal sequences usually contain a hydrophobic core of about 4–15 amino acids, which is often immediately preceded by a basic amino acid. At the carboxyl-terminal end of the signal peptide there are a pair of small, uncharged amino acids separated by a single intervening amino acid that defines the signal peptide cleavage site (see, e.g., von Heijne (1990) J. Membrane Biol. 115:195–201).

A fusion protein can optionally contain other amino acid sequences, in addition to the first and second amino acid sequences, that carry out substantially the same functions as the first and/or second amino acid sequences. For example, a fusion protein can contain an additional member of a specific binding pair and/or an additional amino acid sequence against which an antibody is generated. Thus, a single fusion protein can contain, in addition to the second amino acid sequence, a plurality of sequences derived from different proteins (or multiple epitopes derived from the same protein) and can thus be used to generate antibodies against the different sequences.

A fusion protein can optionally contain an amino acid sequence that permits the cleavage of the fusion protein. For example, a protein cleavage site can be placed between the first and second amino acid sequences. Such a cleavage site can permit the separation of the first amino acid sequence from the second amino acid sequence following purification of the fusion protein. For example, the fusion protein can contain a sequence of amino acids that includes a specific recognition site for enzymatic cleavage which does not occur elsewhere in the molecule. Examples of useful sites are the sequences that are recognized and cleaved by blood factor Xa or enterokinase. A cleavage enzyme can thus by chosen by reference to its recognition sequence.

A fusion protein can optionally contain one or more linker sequences. A linker sequence can be used to provide spacing and/or orientation to the first and/or second amino acid sequences and promote the biological functioning of each of the sequences. A linker sequence generally separates two sequences by a distance sufficient to ensure that each folds into its secondary structure. A linker sequence length of about 20 amino acids can be used to provide a suitable separation of functional protein domains, although longer or shorter linker sequences can also be used (e.g., lengths of 3 to 100 amino acids). Amino acid sequences useful as linkers include, but are not limited to, $(SerGly_4)_y$ (SEQ ID NO:1) wherein y is at least 2, or $Gly_4SerGly_5Ser$ (SEQ ID NO:2). A preferred linker sequence has the formula $(SerGly_4)_4$ (SEQ ID NO:3). Another preferred linker has the sequence $((Ser_4Gly)_3$-Ser-Pro) (SEQ ID NO:4). Alternatively, a fusion protein can lack linker sequences.

The invention also encompasses methods that use an isolated nucleic acid that encodes a protein. An "isolated" nucleic acid is a nucleic acid molecule the structure of which is not identical to that of a naturally occurring nucleic acid or to that of any fragment of a naturally occurring genomic nucleic acid spanning more than one gene. In these embodiments, the protein encoded by the nucleic acid need not be a fusion protein and can contain a sequence that is identical to all or a portion of the amino acid sequence of a naturally occurring protein. Preferably, the protein contains an amino acid sequence that is identical to at least 6, 10, 25, 50, 100, or 200 consecutive amino acids of a naturally occurring protein.

Nucleic acid constructs can be prepared using conventional molecular biology techniques. A nucleic acid can be operatively linked to regulatory elements that direct expression of the coding sequence. These regulatory elements include, but are not limited to, inducible and non-inducible promoters, enhancers, and other elements which are known to those skilled in the art and which drive or otherwise regulate gene expression. Such regulatory elements include but are not limited to the cytomegalovirus (CMV) immediate early gene, a retroviral LTR promoter, and the early or late promoters of SV40. In a preferred embodiment, expression of the nucleic acid is under the control of a human CMV immediate early promoter.

Nucleic acid constructs are preferably incorporated into a vector, e.g., an expression vector such as a plasmid or a viral vector. Specific initiation signals may also be required for efficient translation of nucleic acid molecules. These translational control signals include the ATG initiation codon and adjacent sequences (e.g., sequences that conform with the Kozak consensus sequence). Furthermore, the initiation codon must be in phase with the reading frame of the desired coding sequence to ensure translation of the entire insert. Translational control signals and initiation codons can be of a variety of origins, both natural and synthetic. The efficiency of expression may be enhanced by the inclusion of appropriate transcription enhancer elements, transcription terminators, or introns (see Bittner et al. (1987) Methods Enzymol 153:516).

In Vivo Production of Proteins

A protein, e.g., a fusion protein, is produced by administering a nucleic acid described herein to an animal, e.g., a mammal such as a mouse, rat, goat, rabbit, or human. Following administration of the nucleic acid, translation (as well as transcription, if the nucleic acid is a DNA sequence) occurs in vivo and the protein is thus produced within the animal. The nucleic acid can be administered to the animal by a variety of routes, e.g., intravenously, intramuscularly, intraarterially, intradermally, intraperitoneally, intranasally, or subcutaneously.

The nucleic acid can be "naked" or complexed with a delivery vehicle. Examples of useful delivery vehicles include but are not limited to microparticles, liposomes, ISCOMS, or any other suitable delivery vehicles. For a description of useful methods of gene transfer, see, e.g., Templeton et al. (1997) Nature Biotechnology 15:647–652 and U.S. Pat. No. 6,214,804.

One particularly useful means of obtaining high level expression of a nucleic acid in an animal is by use of a hydrodynamics-based transfection procedure (see, e.g., Liu et al. (1999) Gene Therapy 6:1258–1266; Zhang et al. (1999) Human Gene Therapy 10:1735–1737; Zhang et al. (2000) Gene Therapy 7:1344–1349; He et al. (2000) Human Gene Therapy 11:547–554). According to these methods, a large volume of liquid containing a nucleic acid of interest is injected rapidly into an animal. This method can result in gene expression within 8–24 hours as well as extended gene expression over days or weeks. For example, the injection into the tail vain of a mouse of approximately 1.5 to 2.5 ml of a solution containing about 5–25 ug of plasmid DNA at a rate of approximately 0.3 ml/second can result in expression of the protein encoded by the nucleic acid. If the nucleic acid construct encodes a sequence that directs secretion of the protein, e.g., a signal peptide sequence, then significant amounts of the protein are secreted into the blood of the animal.

The production of a protein in an animal, as described herein, can be accompanied by the administration to the animal of a protease inhibitor or a plurality of different protease inhibitors. Examples include inhibitors of serine, cysteine, or aspartic proteases as well as inhibitors of aminopeptidases. The administration of protease inhibitors to the animal can increase the yield of functional protein isolated from the animal. The protease inhibitors can be administered before, during, or after the administration of the nucleic acid to the animal.

Once the protein is produced within the animal, a biological sample containing the protein can be removed from the animal. As described above for the hydrodynamics-based transfection procedure (e.g., as carried out together with the in vivo administration of protease inhibitors), significant amounts of the protein are produced within about 8–24 hours following the administration of the nucleic acid. The animal may need to be sacrificed, depending upon the nature of the sample to be removed. For example, the protein can be found within the blood or a solid organ including but not limited to the liver, kidney, spleen, heart, and/or lung. Following the removal of a solid organ, a tissue lysate may optionally be prepared to facilitate isolation and processing of the protein. In some embodiments, the biological sample removed from the animal contains at least 5 $\mu$g, 25 $\mu$g, 50 $\mu$g, 200 $\mu$g, 500 $\mu$g, 1 mg, 5 mg, or more of the protein.

Purification of Fusion Proteins

Following the removal of a biological sample containing a fusion protein from an animal, an in vitro method can be carried out to purify the fusion protein. As described herein, the fusion protein contains a first member of a specific binding pair. The biological sample is brought into contact with a second member of the specific binding pair, and the fusion protein contained within the sample is thereby bound to the second member. Unbound material contained within the biological sample can be removed by washing. Methods of immobilizing proteins by means of interactions between members of specific binding pairs are well known to those of skill in the art. As described herein, the second member of the specific binding pair can include proteins such as antibodies as well as non-protein affinity reagents such as nickel (for use in purifying proteins containing a poly histidine tag).

In one example, a fusion protein is captured by using antibodies (specific to the second amino acid sequence of the fusion protein) coated on a solid phase surface. Monoclonal or polyclonal antibodies (in general, it derived from the same animal species as that used for immunization) specific for the second amino acid sequence can be immobilized on a suitable solid phase surface by various methods known to those in the art. In a preferred embodiment of the present invention, human immunoglobulin Fc constant gamma-1 (Cr1) specific antibodies are used. The solid phase surface is not limited to any particular form and includes plastic tubes, microtiter plates, beads such as cellulose beads and agarose beads, latex particles, magnetic particles, paper, and dipsticks. Methods for immobilizing antibodies include passive absorption, covalent linkage, and physical trapping. The fusion protein is captured on the solid phase surface by incubation of the fusion protein-containing biological sample (e.g., sera or tissue lysates) with second amino acid sequence-specific antibodies pre-immobilized on the surface. Unbound materials can be removed by washing.

The immobilized fusion protein can be purified and used to immunize an animal to generate antibodies (immunization methods are described in further detail in subsequent sections). The fusion protein or a portion thereof can optionally be purified to homogeneity following the immobilization and washing steps. As described herein, the fusion protein can optionally contain a sequence, e.g. a sequence located between the first and second amino acid sequences, that permits cleavage of the fusion protein and the isolation of the first amino acid sequence and use for immunization of an animal to generate antibodies.

Alternatively, the fusion protein can be removed from a first animal and used for immunization of a second animal without purification from the biological sample in which it is contained.

The fusion protein can optionally be produced in the same animal strain (e.g., BALB/c mice) that is used for antibody generation. Because of the genetic identity of the animals used in each phase of the method, the fusion protein produced in the first animal need not be purified (or purified to homogeneity) to be useful for the immunization procedure in the second animal. Because any contaminating proteins contained in the biological sample from the first animal will be treated as self-antigens in the immunized animal, only the fusion protein encoded by the nucleic acid will induce a humoral immune response.

Generation of Antibodies

For the immunization process, a protein described herein is administered to an animal, e.g., a mammal such as a mouse, rat, goat, rabbit, or human. The protein, e.g., a fusion protein, can be partially purified, purified to homogeneity, or can be used for immunization without purification from the biological sample in which it is contained. In addition to a fusion protein produced as described herein, a portion of a fusion protein (e.g., produced following cleavage of the fusion protein) can alternatively be used for immunization.

The administration of the protein to the animal results in the generation of an immune response within the animal directed against an amino acid sequence of the protein. This immune response can be exploited to prepare antibodies, either polyclonal or monoclonal, that recognize the amino acid sequence, e.g., the first amino acid sequence of a fusion protein. The protein is delivered by a route and in a dosage that is sufficient to induce a humoral immune response. For example, the protein can be administered intraperitoneally, intravenously, intramuscularly, intraarterially, intradermally, intranasally, or subcutaneously.

The following is an illustrative embodiment of a method of preparing a polyclonal or monoclonal antibody using a protein described herein. A protein, e.g., a fusion protein, is isolated from protein-containing sera or tissue lysate and is mixed with complete Freund's adjuvant or aluminum hydroxide in a 1:1 ratio and injected into a mouse at a dose of at least 1 microgram protein per mouse. Boost injections with the same dose and through the same route are performed at day 9 and day 18. The titer of the polyclonal serum can be determined using an assay described herein. If the titer of the polyclonal serum is satisfactory at day 25, then a third boost is performed at day 26, and the sera will be harvested thereafter or a cell fusion to produce a hybridoma can be performed at day 31.

Monoclonal antibodies can be produced by applying, for example, the well known cell fusion method of Kohler and Milstein ((1976) European Journal of Immunology 6:511–519) to produce hybridomas secreting the desired antibodies in the culture supernatants. After obtaining a homogenous population of cells, which is usually done by limiting dilution cloning, the antibody producing hybridomas are grown in vitro or in vivo and the specificity of a monoclonal antibody can then be characterized.

Screening for Antibodies

As described herein, a protein, e.g., a fusion protein, can be produced within an animal and subsequently immobilized via an interaction between members of a specific binding pair. These rapid and efficient methods of producing and immobilizing a protein containing any sequence of interest (the first amino acid sequence) can be used to screen for antibodies that bind to the first amino acid sequence and/or inhibit the ability of a ligand to bind to the first amino acid sequence. These methods are particularly well adapted for high throughput screening for antibodies that specifically bind to the first amino acid sequence portion of the fusion protein. In addition to or as part of a screening system, the methods of the invention include the identification, quantitation, and/or purification of antibodies.

In one method of the invention, recombinant target protein antigen is used to screen for target protein-specific antibodies. Following the production of antibodies within the animal, test serum can be collected and screened as described herein.

Screening assays can be conducted in a variety of ways. For example, one method to conduct such an assay involves anchoring the protein onto a solid phase (by the binding of the members of a specific binding pair) and detecting protein/antibody complexes anchored on the solid phase at the end of the reaction. In one embodiment of such a method, the protein is anchored onto a solid surface, and the antibody, which is not anchored, is labeled, either directly or indirectly.

As described herein for the immobilization of the fusion protein, a wide variety of solid phases can be used for the immobilization and screening processes. For example, microtiter plates can conveniently be utilized as the solid phase. The second member of the specific binding pair, e.g., a monoclonal antibody, can be immobilized to the solid phase by a non-covalent or covalent attachment. Non-covalent attachment can be accomplished by simply coating the solid surface with a solution containing the second member of the specific binding pair. The surfaces can be prepared in advance and stored.

In order to conduct the assay, the antisera or antibody containing culture supernatant is added to a surface containing the protein. After the reaction is complete, unbound components are removed (e.g., by washing) under conditions such that any complexes formed will remain immobilized on the solid surface. The detection of complexes anchored on the solid surface can be accomplished in a number of ways. Where the previously non-immobilized target binding antibodies are not pre-labeled, an indirect label can be used to detect complexes anchored on the surface, e.g., using a labeled antibody specific for the previously non-immobilized target binding antibody (the antibody, in turn, may be directly labeled or indirectly labeled with a labeled anti-Ig antibody).

Alternatively, a reaction can be conducted in a liquid phase, the bound products separated from unbound components, and complexes detected, e.g., using an immobilized antibody specific for the protein to anchor any complexes formed in solution, and a labeled antibody specific for the target binding antibody of the possible complex to detect anchored complexes.

The incubation times and temperatures for these procedures are not narrowly critical. For example, incubation times can range from 10 minutes to 48 hours, and preferably these are carried out from 1 to 2 hours. The incubation temperatures can range from 4° C. to 37° C. Preferred incubation temperatures are 20° C. to 37° C.

The protein is captured by incubation of protein-containing sera or tissue lysate with specific antibodies pre-immobilized on a surface. After removal of unbound non-specific substances, the testing antibodies are incubated with the solid phase and target protein specific antibodies are quantitatively detected with a binding partner that is labeled or tagged with a signal generating marker. For example, if the testing sera is derived from mouse, the binding partner can be signal generating marker-labeled antibodies specific to mouse IgG antibodies.

In this one embodiment of the present invention, the binding partner can be labeled or tagged with a variety of signal generating markers. These include (but are not limited to) enzymes, chemiluminescent compounds, fluorescent labels, dyes, radioisotopic labels, enzyme cofactors, and biotin. The chemical linkage of this binding partner to a signal-generating marker can be accomplished by a variety of methods known to those in the art.

The following are examples of the practice of the invention. They are not to be construed as limiting the scope of the invention in any way.

EXAMPLES

Example 1

In Vivo Generation of a EGFP-men1-Immunoglobulin Fc Constant Region Fusion Protein-Specific Antibody Response A nucleic acid sequence encoding EGFP-men1 was fused to the human immunoglobulin Fc constant region gamma 1 (Cr1). Ten ug of a DNA construct encoding the EGFP-men1-Cr1 fusion protein was diluted in 2 ml of phosphate buffered saline (PBS) and injected intravenously into a BALB/cj mouse (Jackson Laboratories, Bar Harbor, Me.) within a period of 10 seconds.

The liver was harvested from the mouse 20 hours after injection of the DNA. One hour before harvesting the liver, 100 ul of a protease inhibitor cocktail (Sigma, P8340) was injected intravenously into the mouse. The liver was homogenized and the EGFP-men1-Cr1 fusion protein contained in the lysate was captured on a protein A-bead pre-coated with a Cr1-specific antibody. The mouse anti-Cr1 antibody (a capture antibody) was pre-coated with protein A-bead by an 30 minute incubation of the antibody at a concentration of 20 ug/ml. Immuno-precipitation was done at 4° C. for 2 hours. The precipitates were washed twice with PBS-tween buffer and the amounts of fusion protein was checked with western blot. The isolated fusion protein was then incubated with Al(OH)3 at 4° C. for 2 hours (1 mg alum/125 ug protein). 200 ul of alum/protein mixture was injected subcutaneous into BALB/cj mice. At day 8 and day 23 after first immunization, mice were immunized again with the same procedures. The antisera were harvested and the fusion protein-specific antibody responses were detected.

For antibody detection, a EGFP-containing fusion protein (EGFP-TnIf) was produced as described above. The EGFP-TnIf fusion protein contained in the lysate was captured on a microtiter plate pre-coated with a EGFP-specific rabbit antibody (Invitrogen Inc.). The rabbit anti-EGFP antibody (layer 1; a capture antibody) was immobilized on a microtiter plate (NUNC-Immuno™ plate, MaxiSorp™ Surface) by an overnight incubation of the antibody at a concentration of 2 ug/ml.

The EGFP-TnIf fusion protein (layer 2) was bound to layer 1 by incubating a liver lysate (diluted in 1% BSA and 10% normal goat serum containing blocking buffer) in the wells of the microtiter plate at room temperature for 2 hours. Normal liver lysate which did not contain fusion protein was used in parallel wells as a control for background subtraction. After four washes to remove unbound material, the plates were incubated with a series of dilutions of EGFP-men1-Cr1 fusion protein-specific antisera. The sera derived from luciferase-Cr1 fusion protein immunized mice were used as control antisera. The amount of EGFP-specific antibody (layer 3) bound to the plates was determined by adding the following: biotinylated goat anti-mouse IgG (1/5000) (layer 4); streptavidin-alkaline phosphatase enzyme conjugates (1/10000) (layer 5); and 1 mg/ml p-nitrophenyl phosphate (enzyme substrate), followed by an incubation at 4° C. for 15 hours. The presence of alkaline phosphatase conjugated streptavidin was detected by measuring the absorption at OD 405 nm, after adding the enzyme substrate.

Figure 1:
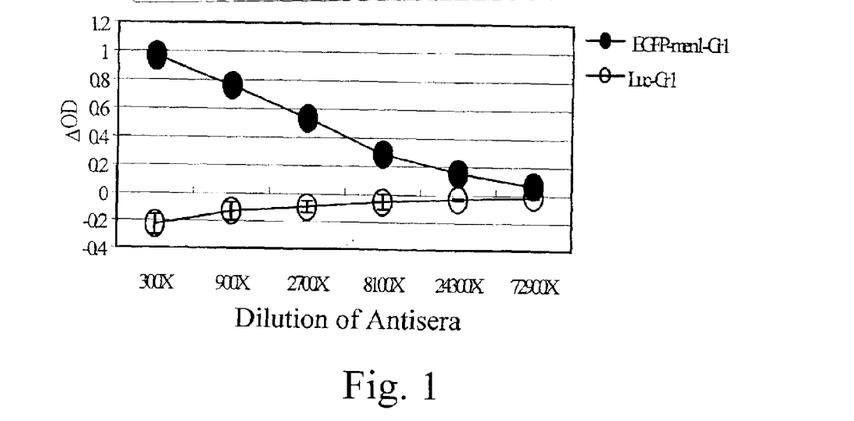
FIG. 1 depicts the generation and detection of Cr1-tagged EGFP fusion protein-specific antibodies from an animal immunized with a nucleic acid encoded Cr1-tagged EGFP fusion protein.

In FIG. 1, the X axis depicts the dilution factor of the antisera (layer 3), and the Y axis depicts delta OD (calculated as the OD derived from fusion protein-containing liver lysates minus the OD derived from normal liver lysates). FIG. 1 shows that the assay detected the presence of target protein-specific antibodies on the microtiter plate and that the delta OD for each dilution of the positive serum displays a linear correlation against the dilution factor. Each point in the figure is an average of triplicate wells and the figure is representative of at least three independent experiments.

Example 2

In Vivo Generation of a Luciferase-Immunoglobulin Fc Constant Region Fusion Protein-Specific Antibody Response A nucleic acid sequence encoding luciferase was fused to the human immunoglobulin Fc constant region gamma 1 (Cr1). Ten ug of a DNA construct encoding the luciferase-Cr1 fusion protein was diluted in 2 ml of phosphate buffered saline (PBS) and injected intravenously into a mouse within a period of 10 seconds.

The liver was harvested from the mouse 20 hours after injection of the DNA. One hour before harvesting the liver, 100 ul of a protease inhibitor cocktail (Sigma, P8340) was injected intravenously into the mouse. The liver was homogenized and the luciferase-Cr1 fusion protein contained in the lysate was captured on a protein A-bead pre-coated with a Cr1-specific antibody. The mouse anti-Cr1 antibody (a capture antibody) was pre-coated with protein A-bead by an 30 minutes incubation of the antibody at a concentration of 20 ug/ml. Immuno-precipitation was done at 4° C. for 2 hours. The precipitates were washed twice with PBS-tween buffer and the amounts of fusion protein was checked with western blot. The isolated fusion protein was then incubated with Al(OH)3 at 4° C. for 2 hours (1 mg alum/125 ug protein). 200 ul of alum/protein mixture was injected subcutaneous into BALB/cj mice. At day 8 and day 23 after first immunization, mice were immunized again with the same procedures. The antisera were harvested and the fusion protein-specific antibody responses were detected.

For luciferase-specific antibody detection, the luciferase recombinant protein (Sigma; layer 2) was coated on the wells of the microtiter plate at room temperature for 2 hours. Irrelevant recombinant protein, lipoprotein lipase, was used in parallel wells as a control for background subtraction. After two washes to remove unbound material, the plates were incubated with blocking buffer containing 1% BSA and 10% normal goat serum for 2 hours. After four washes, the plates were incubated with serial dilutions of luciferase-specific antisera. The sera derived from EGFP-men1-Cr1 fusion protein immunized mice were used as control antisera. The amount of antibody (layer 3) bound to the plates was determined by adding the following: biotinylated goat anti-mouse IgG (1/5000) (layer 4); streptavidin-alkaline phosphatase enzyme conjugates (1/10000) (layer 5); and 1 mg/ml p-nitrophenyl phosphate (enzyme substrate), followed by an incubation at 4° C. for 15 hours. The presence of alkaline phosphatase conjugated streptavidin was detected by measuring the absorption at OD 405 nm, after adding the enzyme substrate.

Figure 2:
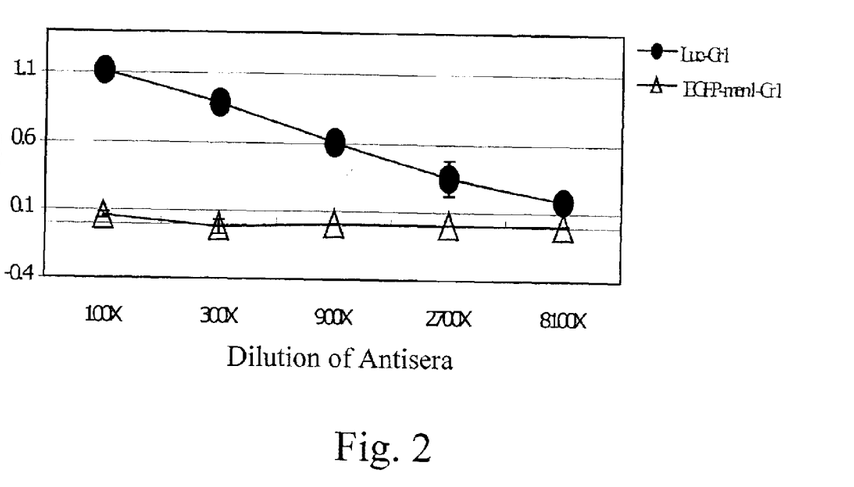
FIG. 2 depicts the generation and detection of Cr1-tagged luciferase fusion protein-specific antibodies from an animal immunized with a nucleic acid encoded Cr1-tagged luciferase fusion protein.

In FIG. 2, the X axis depicts the dilution factor of the test serum (layer 3), and the Y axis depicts delta OD (calculated as the OD derived from fusion protein-containing liver lysates minus the OD derived from normal liver lysates). FIG. 2 shows that the assay detected the presence of target protein-specific antibodies on the microtiter plate and that the delta OD for each dilution of the positive serum displays a linear correlation against the dilution factor. Each point in the figure is an average of triplicate wells and the figure is representative of at least three independent experiments.

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A method of generating an antibody, the method comprising:
   administering to a first mammal a nucleic acid encoding a fusion protein and expressing the fusion protein in the first mammal, wherein the fusion protein contains a first amino acid sequence and a second amino acid sequence, wherein the second amino acid sequence contains a first member of a specific binding pair, and wherein the nucleic acid is administered to the first mammal intravenously, intramuscularly, intraarterially, intradermally, intraperitoneally, intranasally, or subcutaneously;
   removing from the first mammal a biological sample that contains the fusion protein;
   binding a second member of the specific binding pair to the fusion protein via the first member of the specific binding pair to thereby isolate the fusion protein from the biological sample; and
   administering to a second mammal the fusion protein or a portion thereof comprising the first amino acid sequence, to thereby generate an antibody response in the second mammal against the first amino acid sequence of the fusion protein.

2. The method of claim 1, further comprising cleaving the first amino acid sequence from the second amino acid sequence following the isolation of the fusion protein from the biological sample.

3. The method of claim 2, wherein the isolation of the fusion protein from the biological sample comprises immobilizing the fusion protein on a solid phase surface.

4. The method of claim 1, wherein the first member of the specific binding pair is an Fc domain of an immunoglobulin.

5. The method of claim 4, wherein the second member of the specific binding pair is an antibody.

6. The method of claim 5, wherein the antibody is a monoclonal antibody.

7. The method of claim 4, wherein the isolation of the fusion protein from the biological sample comprises immobilizing the fusion protein on a solid phase surface.

8. The method of claim 1, wherein the biological sample is serum.

9. The method of claim 1, further comprising generating a lysate of the biological sample.

10. The method of claim 1, wherein the second member of the specific binding pair is an antibody.

11. The method of claim 10, wherein the antibody is a monoclonal antibody.

12. The method of claim 1, wherein the isolation of the fusion protein from the biological sample comprises immobilizing the fusion protein on a solid phase surface.

13. The method of claim 1, wherein the first member of the specific binding pair is a peptide of at least five amino acids in length.

14. The method of claim 1, wherein the first amino acid sequence is identical to all or a portion of a naturally occurring human protein.

15. The method of claim 14, wherein the first amino acid sequence is at least 25 amino acids in length.

16. The method of claim 14, wherein the first amino acid sequence is at least 50 amino acids in length.

17. The method of claim 14, wherein the first amino acid sequence is at least 100 amino acids in length.

18. The method of claim 1, further comprising isolating from the second mammal antisera containing an antibody that specifically binds to the first amino acid sequence of the fusion protein, wherein the antibody is produced in the second mammal following the administration of the fusion protein or a portion thereof comprising the first amino acid sequence.

19. The method of claim 1, further comprising, following the administration to the second mammal of the fusion protein or a portion thereof comprising the first amino acid sequence, removing a B lymphocyte from the second mammal and fusing the B lymphocyte in vitro with a second cell to form a hybridoma, wherein the hybridoma produces a monoclonal antibody that specifically binds to the first amino acid sequence of the fusion protein.

20. The method of claim 1, further comprising removing components of the biological sample that are not bound to the second member of the specific binding pair, to thereby provide a purified fusion protein.

21. The method of claim 1, wherein the wherein the nucleic acid is administered to the first mammal intravenously.

22. The method of claim 1, wherein the wherein the nucleic acid is administered to the first mammal intramuscularly.

23. The method of claim 1, wherein the wherein the nucleic acid is administered to the first mammal subcutaneously.

24. The method of claim 1, wherein the first amino acid sequence is at least 25 amino acids in length.

25. The method of claim 1, wherein the first amino acid sequence is at least 50 amino acids in length.

26. The method of claim 1, wherein the first amino acid sequence is at least 100 amino acids in length.

27. A method of generating an antibody, the method comprising:

administering to a first mammal an isolated nucleic acid encoding a protein and expressing the protein in the first mammal, wherein the isolated nucleic acid is administered to the first mammal intravenously, intramuscularly, intraarterially, intradermally, intraperitoneally, intranasally, or subcutaneously;

removing from the first mammal a biological sample that contains the protein; and administering to a second mammal the protein or a portion thereof, to thereby generate an antibody response in the second mammal against the protein.

28. The method of claim 27, wherein the protein is a fusion protein.

29. The method of claim 28, wherein the fusion protein contains a first amino acid sequence and a second amino acid sequence, wherein the second amino acid sequence contains a first member of a specific binding pair, and wherein the antibody response is generated against the first amino acid sequence.

30. The method of claim 29, wherein the first member of the specific binding pair is an Fc domain of an immunoglobulin.

31. The method of claim 29, wherein the first member of the specific binding pair is a peptide of at least five amino acids in length.

32. The method of claim 27, wherein the biological sample is serum.

33. The method of claim 27, further comprising generating a lysate of the biological sample.

34. The method of claim 27, further comprising isolating from the second mammal antisera containing an antibody that specifically binds to the protein, wherein the antibody is produced in the second mammal following the administration of the protein.

35. The method of claim 27, further comprising, following the administration to the second mammal of the protein, removing a B lymphocyte from the second mammal and fusing the B lymphocyte in vitro with a second cell to form a hybridoma, wherein the hybridoma produces a monoclonal antibody that specifically binds to the protein.

36. The method of claim 27, wherein the wherein the isolated nucleic acid is administered to the first mammal intravenously.

37. The method of claim 27, wherein the wherein the isolated nucleic acid is administered to the first mammal intramuscularly.

38. The method of claim 27, wherein the wherein the isolated nucleic acid is administered to the first mammal subcutaneously.

* * * * *

UNITED STATES PATENT AND TRADEMARK OFFICE
CERTIFICATE OF CORRECTION

PATENT NO. : 6,800,462 B2  
APPLICATION NO. : 10/077210  
DATED : October 5, 2004  
INVENTOR(S) : Chung-Hsiun Wu, Rong-Hwa Lin and Pei-Ling Hsu Page 1 of 1

It is certified that error appears in the above-identified patent and that said Letters Patent is hereby corrected as shown below:

Cover page, right column
"Swimbanks et al.," replace "Swimbanks" with -- Swinbanks --

Column 14,
Line 53, delete "wherein the" after "wherein the"
Line 56, delete "wherein the" after "wherein the"
Line 59, delete "wherein the" after "wherein the"

Column 16,
Line 17, delete "wherein the" after "wherein the"
Line 20, delete "wherein the" after "wherein the"
Line 23, delete "wherein the" after "wherein the"

Signed and Sealed this

Fifth Day of February, 2008

JON W. DUDAS  
*Director of the United States Patent and Trademark Office*

UNITED STATES PATENT AND TRADEMARK OFFICE
CERTIFICATE OF CORRECTION

PATENT NO. : 6,800,462 B2  
APPLICATION NO. : 10/077210  
DATED : October 5, 2004  
INVENTOR(S) : Chung-Hsiun Wu, Rong-Hwa Lin and Pei-Ling Hsu It is certified that error appears in the above-identified patent and that said Letters Patent is hereby corrected as shown below:

Title page, (56) right column line 4  
"Swimbanks et al.," replace "Swimbanks" with -- Swinbanks --

Column 14,  
Line 53, delete "wherein the" after "wherein the"  
Line 56, delete "wherein the" after "wherein the"  
Line 59, delete "wherein the" after "wherein the"

Column 16,  
Line 17, delete "wherein the" after "wherein the"  
Line 20, delete "wherein the" after "wherein the"  
Line 23, delete "wherein the" after "wherein the"

Signed and Sealed this

Twelfth Day of February, 2008

JON W. DUDAS  
*Director of the United States Patent and Trademark Office*

SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Linker sequence

<400> SEQUENCE: 1

Ser Gly Gly Gly Gly Ser Gly Gly Gly Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Linker sequence

<400> SEQUENCE: 2

Gly Gly Gly Gly Ser Gly Gly Gly Gly Ser
1               5                   10

<210> SEQ ID NO 3
<211> LENGTH: 20
<212> TYPE: PRT
<213> ORGANISM: Artificial Sequence
<220> FEATURE:
<223> OTHER INFORMATION: Linker sequence

<400> SEQUENCE: 3

Ser Gly Gly Gly Gly Ser Gly Gly Gly Gly Ser Gly Gly Gly Gly Ser
1               5                   10                  15

-continued

```
Gly Gly Gly Gly
            20

<210> SEQ ID NO 4
<211> LENGTH: 17
<212> TYPE: PRT
<213> ORGANISM: Artificial Sequence
<220> FEATURE:
<223> OTHER INFORMATION: Linker sequence

<400> SEQUENCE: 4

Ser Ser Ser Ser Gly Ser Ser Ser Ser Gly Ser Ser Ser Ser Gly Ser
1               5                   10                  15

Pro
```